United States Patent [19]

Suzuki et al.

[11] Patent Number: 5,104,511
[45] Date of Patent: Apr. 14, 1992

[54] ELECTROPHORESIS SYSTEM

[75] Inventors: Hideo Suzuki; Nobutaka Kaneko; Akihiko Yamamoto, all of Hachioji; Sadahiro Watanabe, Kunitachi, all of Japan

[73] Assignee: Olympus Optical Co., Ltd., Tokyo, Japan

[21] Appl. No.: 629,486

[22] Filed: Dec. 18, 1990

[30] Foreign Application Priority Data

Dec. 21, 1989 [JP] Japan .................. 1-332370

[51] Int. Cl.⁵ .................. B01D 61/42; B01D 57/02
[52] U.S. Cl. .................. 204/299 R; 204/180.1; 356/344
[58] Field of Search ............ 204/299 R, 182.8, 183.2

[56] References Cited

U.S. PATENT DOCUMENTS 4,578,169  3/1986  Vicario et al. .................. 204/182.8

FOREIGN PATENT DOCUMENTS 61-213658  9/1986  Japan .
62-29954   8/1987  Japan .

Primary Examiner—John Niebling
Assistant Examiner—Caroline Koestner
Attorney, Agent, or Firm—Frishauf, Holtz, Goodman & Woodward

[57] ABSTRACT

In an electrophoresis system, a specimen is analyzed on the basis of a division image obtained by applying the specimen on a substrate and causing an electrophoresis phenomenon to occur. The electrophoresis system comprises a refractometer for measuring the total protein amount of said specimen, a mechanism for applying the specimen onto the head surface of the refractometer, a mechanism for cleaning the head surface of the refractometer, and memory and processing sections for storing the measured data and performing the arithmetic processing with the data obtained on the basis of the division image.

9 Claims, 3 Drawing Sheets

ELECTROPHORESIS SYSTEM

BACKGROUND OF THE INVENTION

1. Field of the Invention

This invention is related to an electrophoresis system for measuring protein division such as serum and total protein amount in the field of clinical testing and the like.

2. Description of the Related Art

A technique is disclosed in the Patent Application Laid-open No. Showa 61-213658 official gazette and others in which a specimen such as serum is applied on a substrate comprised of a cellulose acetate film or the like, and after causing an electrophoresis phenomenon to occur for a predetermined period of time, the specimen is dipped and dyed in a dyeing liquid, decolored and dried, and photometry is performed on the resultant electrophoresis image by means of the measuring light by an interference filter, thereby performing quantitative division. A technique is also disclosed in the Utility Model Publication Application No. Showa 62-29954 official gazette and others in which the protein component for each division is quantitatively analyzed by inputting the total protein amount and a patient number.

However, the traditional electrophoresis system had not the function of measuring the total protein amount, and if it was desired to make use of the protein amount for each division as diagnostic information, the total protein amount was measured by separate measuring means, and that data is inputted to the system, and the protein amount for each division (g/dl) was calculated by multiplying each division rate obtained in the system by the inputted total protein amount, as described in the above-mentioned Utility Model Publication Application No. Showa 62-29954 official gazette.

As described above, it is cumbersome to measure the total protein amount with a separate device and manually input it, and this can also lead to an input error. In addition, in the case that the total protein amount is measured with a separate device, there is also a problem that change of the specimen with time is unavoidable and the measured data become inaccurate.

SUMMARY OF THE INVENTION

It is the object of this invention to provide an electrophoresis system which can also measure the total protein amount along with each division rate.

This invention is characterized, in an electrophoresis system wherein a specimen is analyzed on the basis of the division image obtained by applying the specimen on a substrate and causing an electrophoresis phenomenon to occur, by comprising a refractometer for measuring the total protein amount of the specimen, means for applying the specimen on the head surface of the refractometer, means for cleaning the head surface of the refractometer, and memory and processing means for storing the measured data and performing the arithmetic processing with the data obtained on the basis of the division image.

Further, it is also characterized by comprising a transparent specimen container for containing specimens, means for injecting and mixing a reagent for measuring the total protein amount into a specimen in the specimen container after the picking for obtaining the division image, means for measuring, by colorimetry through the specimen container, the total protein amount of the specimen into which the reagent was mixed, and memory and processing means for storing the measured data and performing the arithmetic processing with the data obtaining on the basis of the division image.

Such construction allows not only the division rate of a specimen by electrophoresis but also the total protein amount of the specimen to simultaneously be measured, and also allows the arithmetic processing of these measured data to be performed without human hands.

BRIEF DESCRIPTION OF THE DRAWINGS

FIGS. 3 and 4 show a modification example of the total protein measuring section, wherein FIG. 3 is a view schematically showing the whole and FIG. 4 is a view showing the measuring mechanism.

DETAILED DESCRIPTION OF THE PREFERRED EMBODIMENTS

Now, the electrophoresis systems related to the embodiments of this invention are described with reference to the attached drawings.

Figure 1:
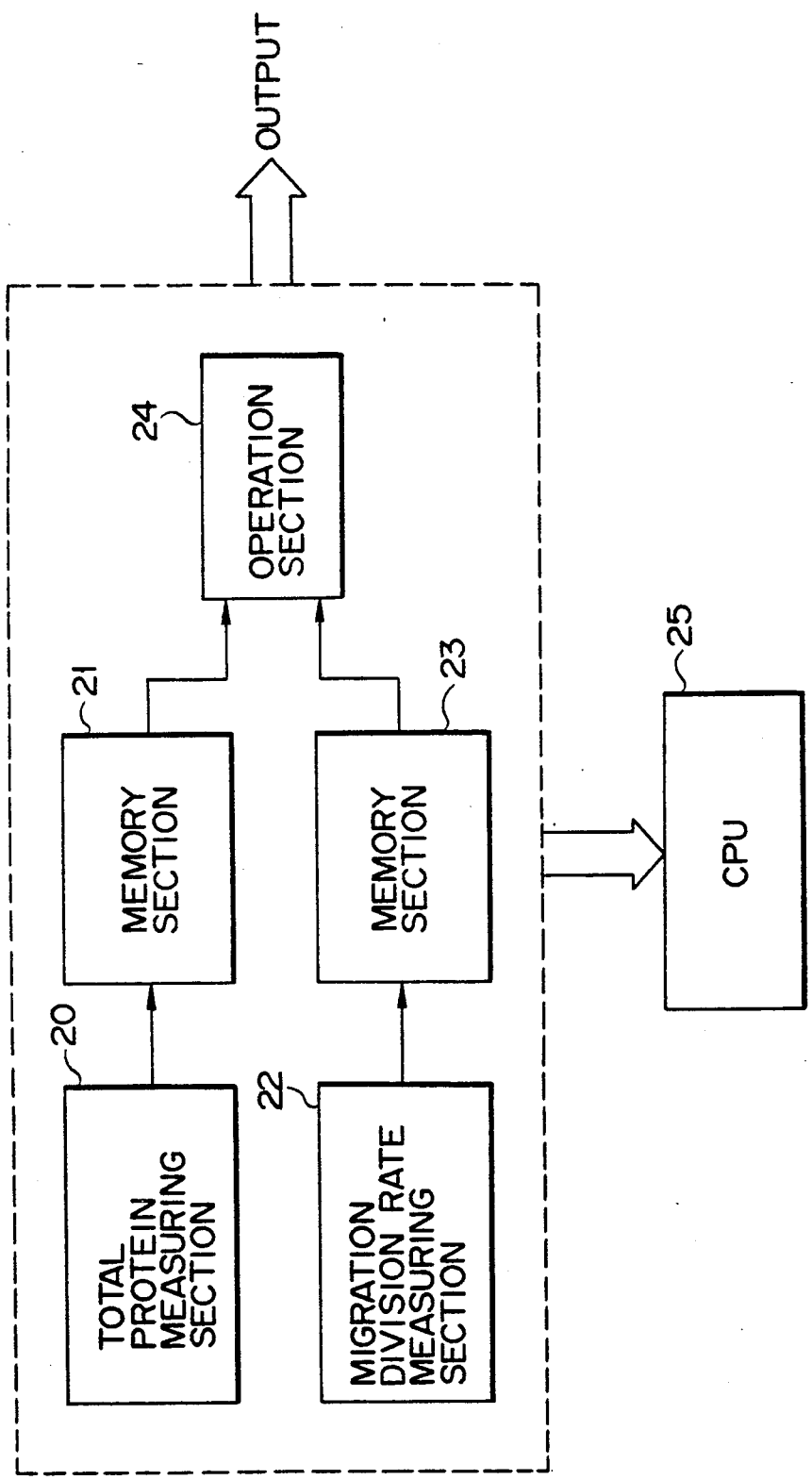
FIG. 1 is a block diagram for schematically showing the whole electrophoresis system related to an embodiment of this invention.

The migration system comprises, as described in FIG. 1, total protein measuring section 20 for measuring total protein from serum, memory section 21 for storing the measured total protein data at total protein measuring section 20, migration division rate measuring section 22 for measuring the division rate due to electrophoresis, memory section 23 for storing the measured division rate data at migration division rate measuring section 22, and arithmetic processing section 24 for performing the arithmetic processing of the total protein data and division rate data to obtain the protein amount for each division (g/dl). The arithmetic processing section 24 may include a memory function.

Next, the total protein measuring section 20 is described with reference to FIG. 2.

In the figure, reference numeral 1 represents a container for containing specimens, in which a plurality of cells 1a-1j for containing a plurality of specimens such as serums are longitudinally disposed. Specimens 2 contained in these cells are divisionally supplied to the total protein measuring section 20 and migration division rate measuring section 22 to measure the total protein amount, division rate, etc.

Part of specimens 2 respectively contained in the cells is applied on a substrate by means of applicator 3 of migration division rate measuring section 22 and an electrophoresis phenomenon is caused to occur, and the division image due to the electrophoresis is optically measured, whereby the division rate and the like for each specimen are obtained. The construction of the migration division rate measuring section may be same as that shown, for instance, in Patent Application Laid-open No. 61-213658, and thus the description thereof is omitted here. The division rate data obtained in the migration division rate measuring section 22 are supplied, after stored in memory section 23 or directly, to arithmetic processing section 24. These sections 20-24 are controlled by CPU 25, and data are outputted from the respective sections as needed.

Figure 2:
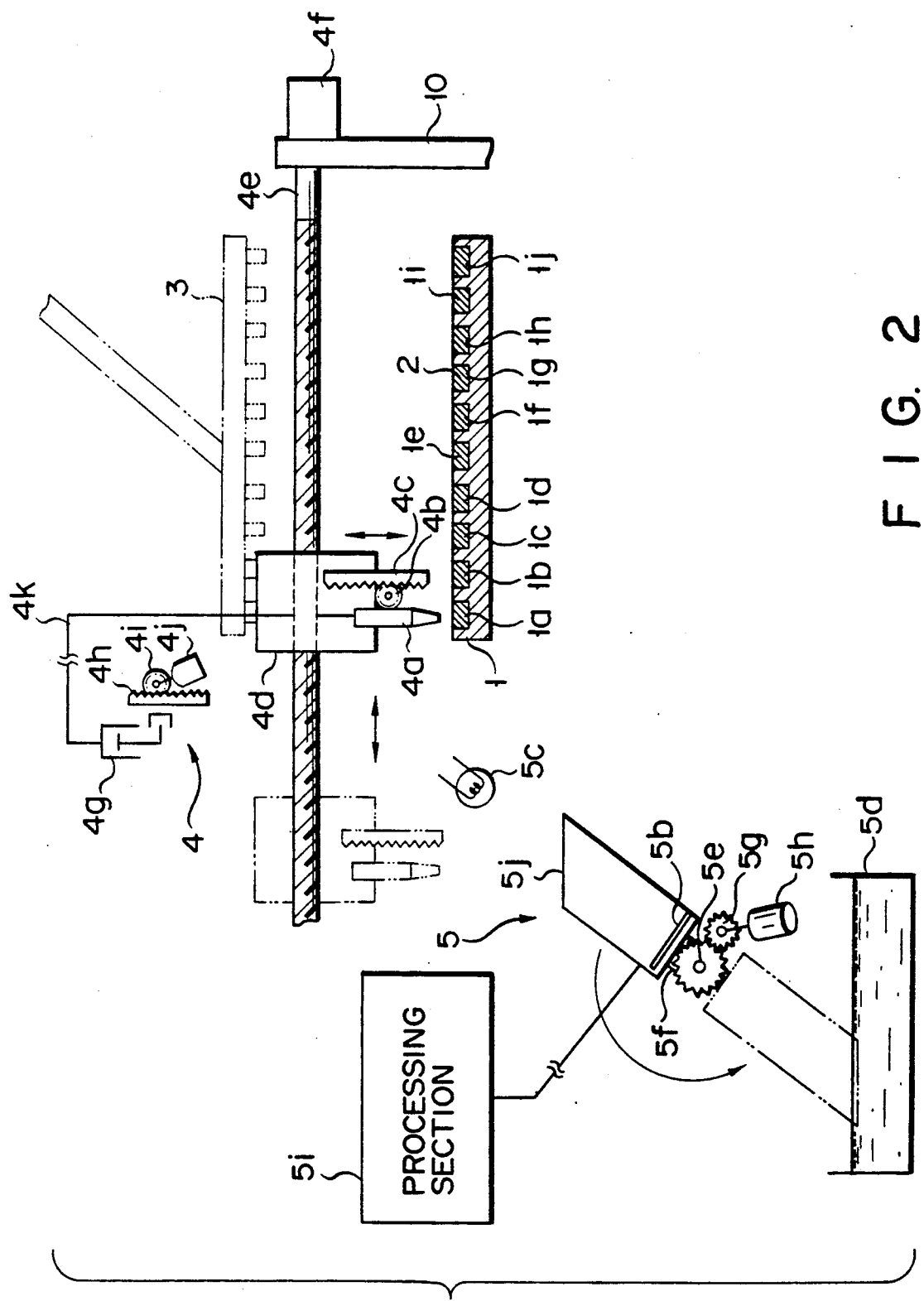
FIG. 2 is a view for schematically illustrating the total protein measuring section of the above-mentioned electrophoresis system.

The total protein measuring section 20 has a mechanism 4 for sampling specimens 2 and measuring mechanism 5 for measuring total protein (TP) as shown in FIG. 2. Pickup mechanism 4 includes a suction and discharge mechanism for picking-up specimen 2 from specimen container 1 by suction and discharging it into measuring mechanism 5, and a drive mechanism for performing the suction and discharge of the suction and discharge mechanism.

The suction and discharge mechanism has nozzle 4a which is disposed above specimen container 1 so that it can suck the specimens 2 contained in the cells of specimen container 1. The nozzle 4a is supported on support 4d movably in the upward and downward directions. To the nozzle 4a, pinion 4b is attached for rotation and a motor (not shown) for rotating the pinion 4b is also attached so that they are vertically movable with nozzle 4a, respectively. Rack 4c which is vertically extending and meshed with pinion 4b is fixed to the support 4d. Thus, nozzle 4a is upwardly and downwardly moved along rack 4c by the rotation of pinion 4b, thereby enabling its tip to be put in and drawn out from the cell. The support 4d is screwed with lead screw 4e which is laterally extending above and along specimen container 1. One end of the lead screw 4e is further extending above measuring mechanism to be described later. The screw 4e is supported for rotation on system main body 10, and it is rotated by reversible motor 4f fixed to system main body 10, centering around the horizontal axis. The support 4d screwed with the screw 4e is prevented from rotating by a stopper (not shown) provided in the system main body, and thus it can be freely moved between above cell 1j at the rear end of specimen container 1 and above the measuring mechanism 5.

The drive mechanism has syringe 4g connected to one end of pipe 4k, the other end of which is connected to the upper end of the support 4d. Rack 4h is fixed to the piston of the syringe 4g, and pinion 4j rotatable by reversible motor 4j is engaged with the rack 4h. Accordingly, driving of motor 4j causes syringe 4g to selectively perform suction or discharge through pipe 4k.

The measuring mechanism 5 has head (prism) 5a of a refractometer provided with inclined coating surface 5j on which specimen 2 is to be applied. Photo detector 5b is mounted in the vicinity of the surface in prism 5a opposite to the coating surface 5j. Lamp 5c which is the TP light source for emitting a measuring light to coating surface 5j is disposed diagonally above the head 5a, and wash liquid bath 5d containing a wash liquid for washing coating surface 5j is disposed below the head 5a. Gear 5e is supported for rotation on the system main body. The gear 5e is provided with projecting support column 5f so that it rotates as the gear rotates, and on the projecting end of the support column 5f, the head 5a is supported at the photo detector 5b side end. Engaged with gear 5e is gear 5g which can be rotated by reversible motor 5h. Thus, head 5a is selectively rotated by nearly 180 degrees by driving the motor 5h between a measuring position at which coating surface 5j faces lamp 5c and a washing position at which coating surface 5j is dipped in the wash liquid within wash liquid bath 5d. The total protein measuring section is constructed as described above. When head 5a is in the measuring position, the specimen applied on coating surface 5j transmits the light from lamp 5c with a transmission rate corresponding to the total protein amount of the specimen, and the photo detector 5b receives the transmitted light. Connected to the photo detector 5b is a processing section 5i which processes the photometry data from photo detector 5b and determines the total protein amount. The measured data from the processing section 5i is sent to the arithmetic processing section 24.

The operation of total protein measuring section 20 with the above-mentioned construction is now described.

First, the lower end of nozzle 4a is dipped in the specimen 2 in the first cell 1a of specimen container 1, motor 4j is driven to put syringe 4g in a suction state, thereby for sucking the specimen 2 into nozzle 4a. By driving a motor, not shown, nozzle 4a is moved above specimen container 1 through pinion 4b. Then, motor 4f is driven to move support 4d to the left side in the figure and position nozzle 4a above head 5a as shown by dotted lines. The motor 4j is now driven in the reverse direction to put syringe 4g in a compression state, thereby dropping and applying the specimen 2 in nozzle 4a onto coating surface 5j of head 5a. By exposing the coating surface 5j to the light of lamp 5c, the total protein amount (TP) of the specimen 2 is determined and calculated by processing section 5i. calculated data are stored in memory section 21 and simultaneously sent to arithmetic processing section 24. The division rate obtained in migration division rate measuring section 22 is also sent to the arithmetic processing section 24, where the total protein amount obtained in total protein measuring section 20 is multiplied by the division rate obtained in migration division rate measuring section 22 to calculate the protein amount for each division. These operations are automatically performed at a predetermined timing by controlling the respective driving sources and circuits by the use of CPU 25 shown in FIG. 1.

When the measurement of the specimen 2 in the first cell 1a is completed, nozzle 4a is moved to the second cell 1b by motor 4f, and the operation similar to the above described operation is performed. In this way, automatic measurement of the protein amount for each division of the specimen in each cell is sequentially performed.

The CPU 25 may be set so that sequentially measured data are previously stored in memory sections 21 and 23, and these are subjected to a collective arithmetic processing in migration division rate measuring section 22.

Although total protein measuring section 20 is constructed in a type using a refractometer in the aforementioned embodiment, another type may be utilized. As an example of this, total protein measuring section 20 by colorimetry is described with reference to FIGS. 3 and 4. In this example, members substantially same as those in the above described embodiment are assigned with the same reference numerals, and the description thereof is omitted or simplified.

Specimen container 1 is formed of a material which transmits the light from lamp 5c, and in this embodiment, it is formed of thick-walled glass or plastic.

Total protein measuring section 20 includes picking and mixing mechanism 6 for picking up a reagent for colorimetry and mixing this reagent into the specimen 2 in a cell, and measuring mechanism 5 for measuring the total protein amount (TP) of the specimen 2.

Picking and mixing mechanism 6 has nozzle 6a for injecting reagent 8 into the specimen and stirring rod 6b for stirring the specimen 2 and reagent 8. Nozzle 6a is fixed to support 6f, and stirring rod 6b is supported by support 6f so that it can move vertically. The stirring rod 6b has a tip end portion to be inserted into specimen 2. and a base end portion supporting the tip end portion for rotation and provided with motor 6e for this rotation. On the base end portion, pinion 6c driven by a motor, not shown, is supported for rotation. Rack 6d fixed to support 6f and extending vertically is engaged with the pinion 6c. Stirring rod 6b is thus vertically moved along rack 6d by rotation of pinion 6c and the tip end thereof can be put in and drawn out from a cell, and it can be rotated in specimen 2 by motor 6e to stir reagent 8. The support 6f is screwed with lead screw 6g which is extending above and along specimen container 1 from the first cell 1a over the last cell 1j. The lead screw 6g is supported for rotation on system main body 10, and it is rotated by reversible motor 6h fixed to system main body 10, centering around the horizontal axis. The motor 6h is preferably a step motor which intermittently rotates depending on the distance between the cells of specimen container 1. Support 6f screwed with the screw 6g is prevented from rotating by a stopper (not shown) provided in the system main body, and thus it can be freely moved between above cell 1a at the front end of specimen container 1 and above cell 1j at the rear end thereof.

One end of pipe 6q is connected to the rear end of the nozzle 6a. The other end of the pipe 6q is inserted in reagent 8 contained in reagent bath 6i. In the middle of the pipe 6q, there are interposed syringe 6l and first and second electromagnetic valves 6j and 6k, which are sandwiching the syringe 6l. Fixed to the syringe 6l is rack 6m, with which pinion 6n rotated by motor 6p is engaged. The electromagnetic valves 6j and 6k and motor 6p are controlled so that electromagnetic valve 6j is opened and then motor 6p is rotated in one direction to such reagent 8 in reagent bath 6i into syringe 6l, and then electromagnetic valve 6k is opened and motor 6p is rotated in the other direction to drop a predetermined amount of reagent 8 in syringe 6l through nozzle 6a into the specimen 2 in a cell of specimen container 1.

Figure 3:
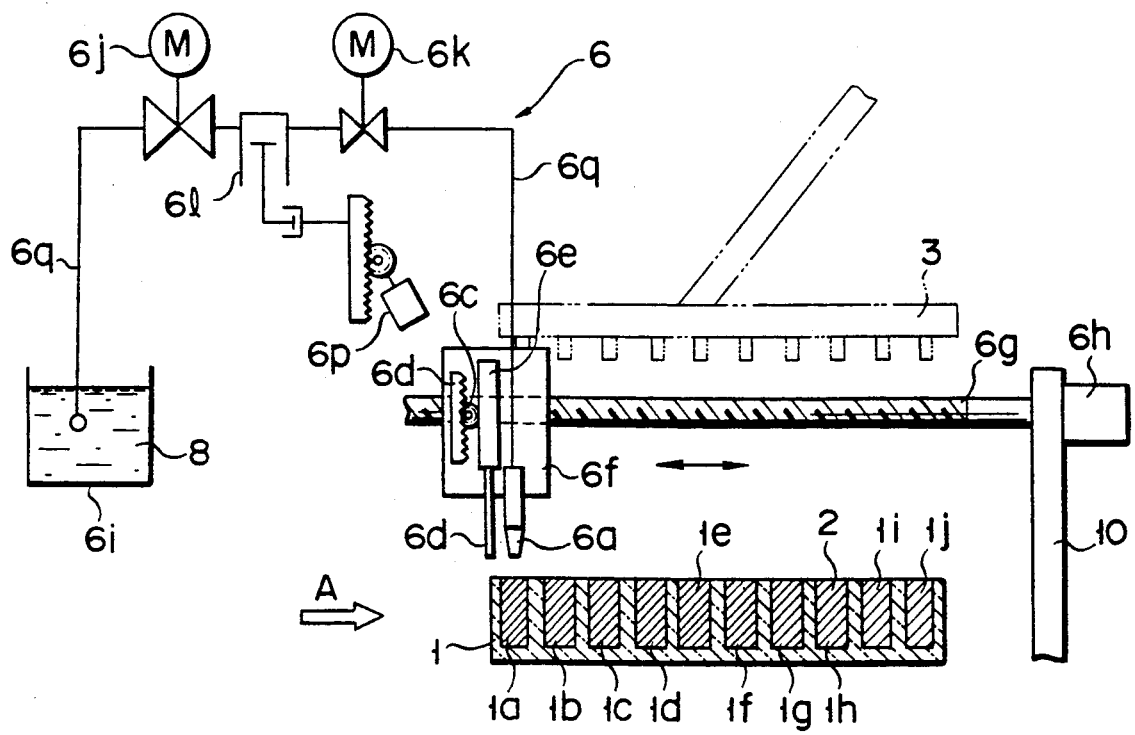
Figure 4:
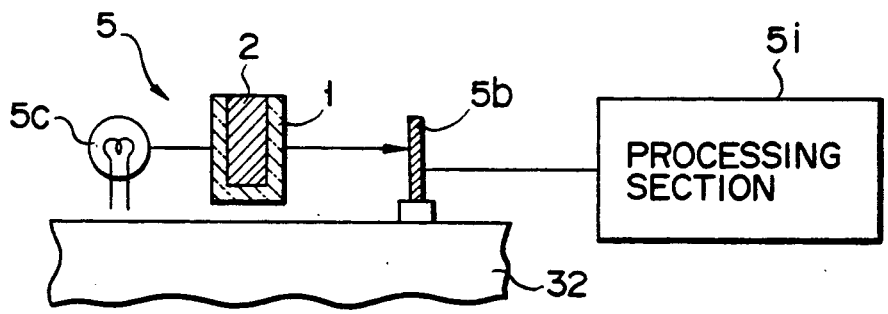

Photo detector 5b and lamp 5c of the measuring mechanism 5 are placed so as to sandwich one cell of transparent specimen container 1, as shown in FIG. 4 viewed from the direction of arrow A in FIG. 3. The photo detector 5b and lamp 5c are supported on moving body 32 which ca be moved along the longitudinal direction of specimen container 1, and they are moved longitudinally of specimen container 1 in conjunction with the traveling of the support 6f so that they sequentially correspond to the cells. In the photo detector 5b, light of a light volume corresponding to the light absorption rate of each specimen 2 is received, and the total protein amount of each specimen is calculated in processing section 5i connected to the photo detector 5b. Based on the calculated data, the protein amount of each division is automatically obtained in the manner described with reference to FIG. 1.

In the above described electrophoresis system related to this invention, not only the electrophoresis division rate of a specimen but also the total protein amount can simultaneously be obtained with this system per se, and, in addition, the arithmetic processing of the protein amount (g/dl) and the like are automatically performed for each division. Thus the analysis result becomes accurate, and labor and time can be saved, whereby the cost performance is improved.

What is claimed is:

1. An electrophoresis system comprising:

protein amount determining means for determining and outputting a total protein amount of a specimen;

migration division rate determining means for determining and outputting a migration division rate of said specimen; and calculating means coupled to both said protein amount determining means and to said migration division rate determining means for calculating a protein amount for each division of said specimen based on the outputs of both said protein amount determining means and said migration division rate determining means;

said protein amount determining means comprising:

a refractometer for measuring the total protein amount of said specimen, said refractometer having a head surface;

means for applying said specimen onto said head surface of said refractometer;

cleaning means for cleaning said head surface of said refractometer; and means for outputting measured protein amount data corresponding to the protein amount measured by said refractometer.

2. The electrophoresis system according to claim 1, further comprising:

a container having a plurality of cells for containing respective specimens; and means including an applicator for applying a part of respective specimens contained in said cells to said migration division rate determining means; and wherein said protein amount determining means determines the total protein amount of respective specimens from a remaining part of respective specimens contained in said cells.

3. The electrophoresis system according to claim 1, further comprising moving means for moving said refractometer between a first position in which said head surface of said refractometer is applied with the specimen and a second position in which said head surface is cleaned by said cleaning means.

4. The electrophoresis system according to claim 3, wherein:

said cleaning means includes a bath containing a wash liquid; and said moving means includes means for rotating said refractometer between said first position where said head surface is apart from the wash liquid in said bath, and said second position where said head surface is dipped in the wash liquid in said bath so that said head surface is cleaned with the wash liquid.

5. The electrophoresis system according to claim 4, wherein:

said head surface of said refractometer comprises a prism surface; and said moving means includes means for rotating said refractometer so that said prism surface is substantially horizontal in both said first and second positions.

6. The electrophoresis system according to claim 1, wherein said cleaning means and said head surface of said refractometer are movable relative to each other, and wherein said cleaning means selectively cleans said head surface at a given relative position of said head surface and said cleaning means.

7. The electroporesis system according to claim 6, further comprising moving means for moving said head surface of said refractometer relative to said cleaning means between a first position in which said head surface is applied with the specimen, and a second position in which said head surface is cleaned by said cleaning means.

8. The electrophoresis system according to claim 7, wherein:

said cleaning means includes a bath containing a wash liquid; and said moving means includes means for rotating said refractometer between said first position where said head surface is apart from the wash liquid in said bath, and said second position where said head surface is dipped in the wash liquid in said bath so that said head surface is cleaned with the wash liquid.

9. The electrophoresis system according to claim 8, wherein:

said head surface of said refractometer comprises a prism surface; and said moving means includes means for rotating said refractometer so that said prism surface is substantially horizontal in both said first and second positions.

* * * * *